United States Patent [19]
Freeman et al.

[11] Patent Number: 5,960,054
[45] Date of Patent: *Sep. 28, 1999

[54] ANGIOGRAPHIC SYSTEM INCORPORATING A COMPUTERIZED TOMOGRAPHIC (CT) SCANNER

[75] Inventors: Kenneth L. Freeman, Stow; John J. Barni, Mayfield Village; David W. Hoffmeyer, Concord; Donald E. Negrelli, Gates Mills; Kim S. Luckner, Mentor; Joseph S. Deucher, Lyndhurst, all of Ohio

[73] Assignee: Picker International, Inc., Highland Heights, Ohio

[*] Notice: This patent issued on a continued prosecution application filed under 37 CFR 1.53(d), and is subject to the twenty year patent term provisions of 35 U.S.C. 154(a)(2).

[21] Appl. No.: 08/978,901

[22] Filed: Nov. 26, 1997

[51] Int. Cl.$^6$ ...................................................... H05G 1/60
[52] U.S. Cl. .................................. 378/4; 378/20; 378/196
[58] Field of Search .................................. 378/196, 4, 20

[56] References Cited

U.S. PATENT DOCUMENTS

| | | | |
|---|---|---|---|
| 4,868,845 | 9/1989 | Koropp | 378/208 |
| 5,199,060 | 3/1993 | Kato . | |
| 5,327,474 | 7/1994 | Inoue et al. | 378/196 |
| 5,448,610 | 9/1995 | Yamamoto et al. . | |
| 5,525,905 | 6/1996 | Mohapatra et al. . | |
| 5,528,655 | 6/1996 | Umetani et al. . | |
| 5,544,212 | 8/1996 | Heuscher . | |
| 5,592,523 | 1/1997 | Tuy et al. . | |

FOREIGN PATENT DOCUMENTS 0 392 716 A1  2/1990  European Pat. Off. .

OTHER PUBLICATIONS

"Percutaneous Vertebroplasty Guided By a Combination of CT and Fluoroscopy" Afshin Gangi, et al., *AJNR* 15:83–86, Jan. 1994.

"The Interventional CT and Fluoroscopy Room" Z.L. Barbaric, MD, et al. Abstract, *Radiology,* Nov., 1996, vol. 201P p. 475.

(List continued on next page.)

*Primary Examiner*—Craig E. Church
*Attorney, Agent, or Firm*—Fay, Sharpe, Beall, Fagan, Minnich & McKee, LLP

[57] ABSTRACT

A gantry (A) has a bore defining a first patient examination region (12). A first x-ray source (B) is mounted to a frame (C) for rotation around the examination region (12). An arc of first radiation detectors (14) detects x-rays which have traversed the examination region. A first image reconstruction processor (18) reconstructs a tomographic image representation from signals generated by the first radiation detectors. An angiographic device (D) is positioned remote from the gantry along a longitudinal axis (25) for generating and displaying angiographic image representations on a display monitor (46). A second examination region is defined along the longitudinal axis (25) between a second x-ray source (36) and an image intensifier tube (38). A second processor (44) reconstructs the angiographic projection image representations from signals generated by the image intensifier tube (38). A C-arm (30) can be suspended from an overhead track (50) for supporting the second x-ray source (36) and the image intensifier tube (38). A common patient support (24–28) extends along the longitudinal axis between the gantry and the angiographic device for positioning a patient within the first and second examination regions. The patient support includes a slide mechanism (60–64) which permits the patient support to be retracted from the gantry. The processors (18, 44) can be a incorporated into a single controller (E) which fuses or combines an image generated by the angiographic imaging subsystem with an image generated by the tomographic imaging subsystem.

8 Claims, 5 Drawing Sheets

OTHER PUBLICATIONS

Large Area, Flat–Panel a–Si:H Arrays for X–Ray Imaging, L.E. Antonuk, et al. SPIE vol. 1896 *Physics of Medical Imaging* (1993).

Development of Hydrogenated Amorphous Silicon Sensors for High Energy Photon Radiotherapy Imaging, L.E. Antonuk, et al. *IEEE Transactions of Nuclear Science*, vol. 37, No. 2, Apr. 1990.

Radiation Imaging with 2D a–Si Sensor Arrays, I. Fujieda, et al. *IEEE Transactions on Nuclear Science*, vol. 39, No. 4, 1992.

Development of Hydrogenated Amorphous Silicon Sensors for Diagnostic X–Ray Imaging, L.E. Antonuk, et al. *IEEE Transactions on Nuclear Science*, vol. 38, No. 2, Apr., 1991.

A High Resolution, High Frame Rate, Flat–Panel TFT Array for Digital X–Ray Imaging, L.E. Antonuk, et al., SPIE vol. 2163 *Physics of Medical Imagaing* (1994).

Digital Radiology Using Self–Scanned Readout of Amorphous Selenium, W. Zhao, et al., SPIE vol. 1896 *Physics of Medical Imaging* (1993).

Amorphous Silicon X–Ray Imaging Sensor, J. Chabbal, et al. SPIE's Symposium "Medical Imaging 1996", 10–15 FCS, Newport Beach.

Swissray Advertisement, *Medical Imaging*, vol. 12, No. 9, Sep., 1997.

Picker International, Orbitor HF Mobile C–Arms Product Data Sheet, 1994.

FischerImaging Product Data Sheet—Ceiling Suspended Imaging System.

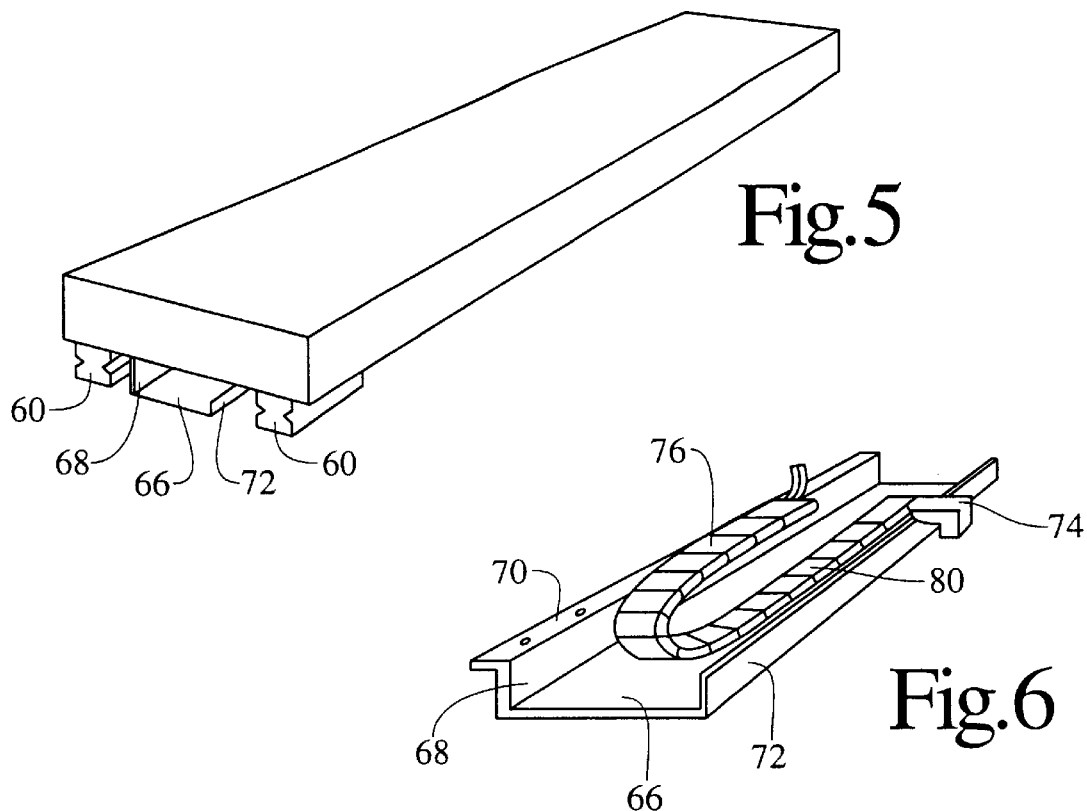
Fig.5
Fig.6
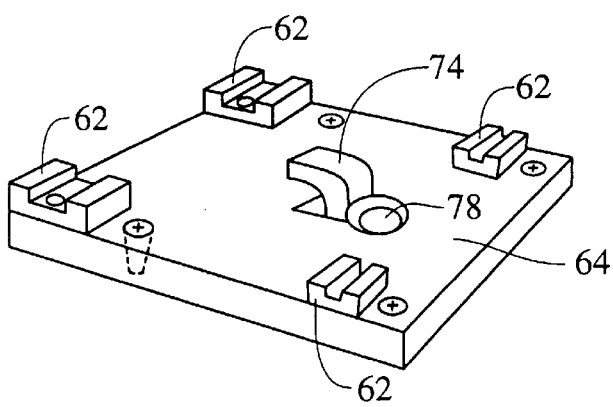
Fig.7
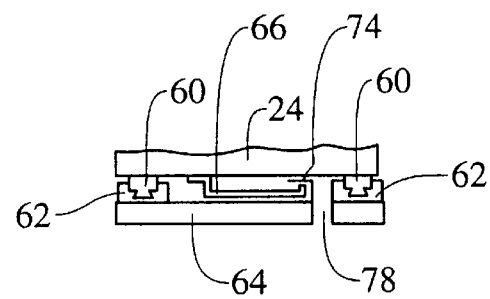
Fig.8

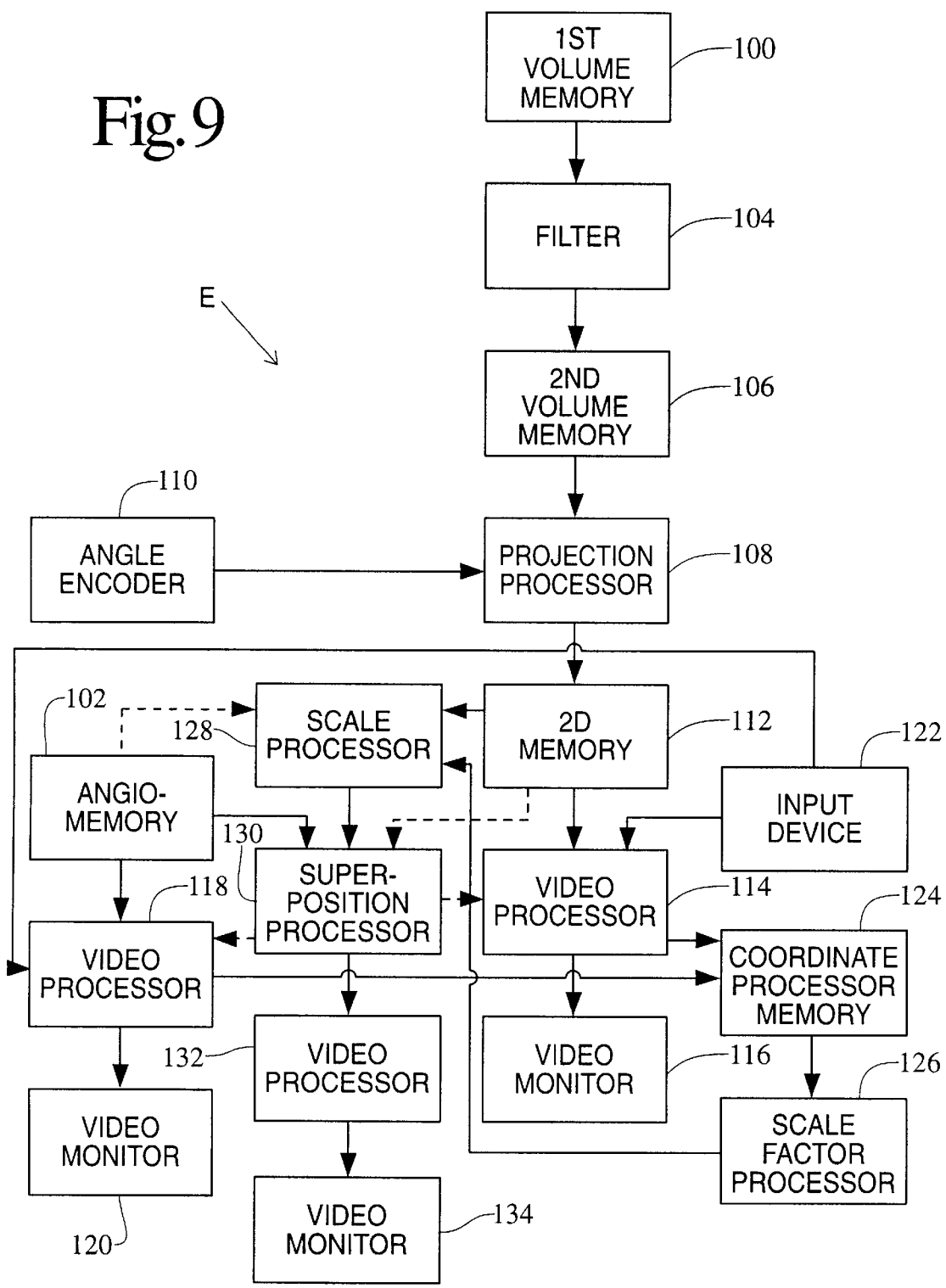

ANGIOGRAPHIC SYSTEM INCORPORATING A COMPUTERIZED TOMOGRAPHIC (CT) SCANNER

BACKGROUND OF THE INVENTION

The present invention relates to the diagnostic imaging arts. It finds particular application in conjunction with an integrated angiographic and computerized tomographic (CT) diagnostic imaging system and will be described with particular reference thereto. However, it should be appreciated that the present invention may also find application in conjunction with other types of multi-modality diagnostic imaging systems.

Conventional x-ray angiography is an examination where a contrast material that is opaque to x-rays is introduced into the blood stream of a patient through a catheter that has been placed in a given vessel. The vessel used depends on where the pathology is suspected to be. Once the catheter is in place the contrast material is injected into the patient's blood stream through the catheter while the patient is exposed to x-rays. The intensity of the x-rays passing through the patient's body are detected on film or detected electronically using a fluorescing screen that is backed by an image intensifier. The resulting image is a superposition of all the anatomical structures in the x-rays' path with the most dense structures appearing brighter than the less dense structures.

It is often necessary to observe many different angles in order to make a diagnosis with an angiographic system. It is known to rotate the x-ray tube and image intensifier in an arc around the patient taking many separate exposures and displaying the composite of all of the two dimensional images in a rotational way causing the resultant views to appear as three dimensional. However, because the image data is analog, the only rendering mode available is Maximum Intensity Projection (MIP). Further, each angle requires an injection of contrast material and a further exposure of radiation to the patient. As the number of radiation exposures increase, the radiation dosage to the patient problematically increases.

One solution has been to use an angiographic system in an angiographic room or suite for needle or catheter placement, and to use a computerized tomographic (CT) scanner located in another room or suite for performing diagnostic imaging while introducing contrast material into the blood stream of the patient. A problem with this solution is that the patient must be transported between separate diagnostic suites which takes time, and which could disturb any catheters and/or sensors which may be connected to the patient. Another problem is that maintaining two separate suites for housing two major pieces of diagnostic equipment is expensive.

Another solution has been to modify a CT patient table to allow a patient to be examined by a standard angiographic unit in one direction and by a CT scanner positioned 90° relative to the angiographic unit within the same suite. An advantage is that the patient does not have to be transferred between suites. However, there are many redundant functions with this solution such as the filming device/imaging system and the display system that drive the cost of maintaining a single suite with a complete angiographic system and a complete CT scanner too high for practical use. Also, having to reposition (i.e. pivot) the patient support ninety degrees causes difficulties in some types of studies.

It is also known to use a portable or mobile C-arm fluoroscopic unit with a standard CT scanner in a CT suite to do biopsy needle guidance and very limited catheter placement work. However, this solution is limited by the inability of portable fluoroscopic units to achieve all the necessary positions for complex catheter placement procedures and insufficient power for x-ray generation.

Accordingly, it has been considered desirable to develop a new and improved angiographic system incorporating a computerized tomographic (CT) scanner which meets the above-stated needs and overcomes the foregoing difficulties and others while providing better and more advantageous results.

SUMMARY OF THE INVENTION

In accordance with one aspect of the present invention, a multi-modality diagnostic imaging system is disclosed. The multi-modality imaging system includes a first diagnostic imaging subsystem including a frame and a bore through the frame defining a first examination region. The first diagnostic imaging subsystem further includes a mechanism for generating volumetric image representations of an object when the object is positioned within the first examination region. A second diagnostic imaging subsystem defines a second examination region, and includes a mechanism for generating angiographic image representations of the object when the object is positioned within the second examination region. The first and second examination regions are located along a common longitudinal axis of the multi-modality imaging system. A support includes a couch which is adapted for movement in either direction along the common longitudinal axis for carrying the object between the first examination region and the second examination region.

In accordance with a second aspect of the present invention, a method of performing a diagnostic imaging procedure with a multi-modality imaging system is disclosed. The imaging system includes a frame defining a first examination region, a tomographic imaging subsystem for generating volumetric image representations of an object positioned within the first examination region, an angiographic imaging subsystem for generating angiographic image representations of an object positioned within a second examination region, and a support adapted for linear movement between the first and second examination regions. The method includes driving the support along a longitudinal axis to position an object within the second examination region, performing an angiographic procedure with the angiographic imaging subsystem, driving the support along the longitudinal axis to position the object within the first examination region, and performing a volumetric imaging procedure with the tomographic imaging subsystem.

One advantage of the present invention is the provision of an multi-modality diagnostic imaging system which incorporates an angiographic subsystem and a diagnostic imaging subsystem which functionally replaces a conventional filmer device.

Another advantage of the present invention is the provision of a multi-modality diagnostic imaging system which reduces the number of x-ray exposures required for an angiographic exam.

Yet another advantage of the present invention is the provision of a multi-modality diagnostic imaging system which utilizes spiral scanning techniques to obtain a volume of data that can be presented in any orientation in a variety of rendering modes including Maximum Intensity Projection, surface shaded display, or compositing, etc.

A further advantage of the present invention is the provision of a multi-modality diagnostic imaging system that combines or fuses an image generated by an angiographic imaging subsystem with an image generated by a tomographic imaging subsystem for display on a single monitor.

Still another advantage of the present invention is the provision of an angiography system which captures all possible angles of view of the anatomy from one contrast injection and one x-ray exposure.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment(s) and are not to be construed as limiting the invention.

FIG. 5 is a perspective view of a sliding mechanism associated with the patient support of FIG. 2;

FIG. 6 is a perspective view of a tray secured to the bottom of the patient support of FIG. 5;

FIG. 7 is a perspective view of a sliding mechanism associated with a floor-mounted plate;

FIG. 8 is an end view showing the patient support of FIG. 5 slidably secured to the floor-mounted plate of FIG. 7; and FIG. 9 is a block diagram of an integrated control processor for either of the multi-modality diagnostic imaging systems of FIGS. 1–8.

DETAILED DESCRIPTION OF THE PREFERRED EMBODIMENT(S)

Figure 1:
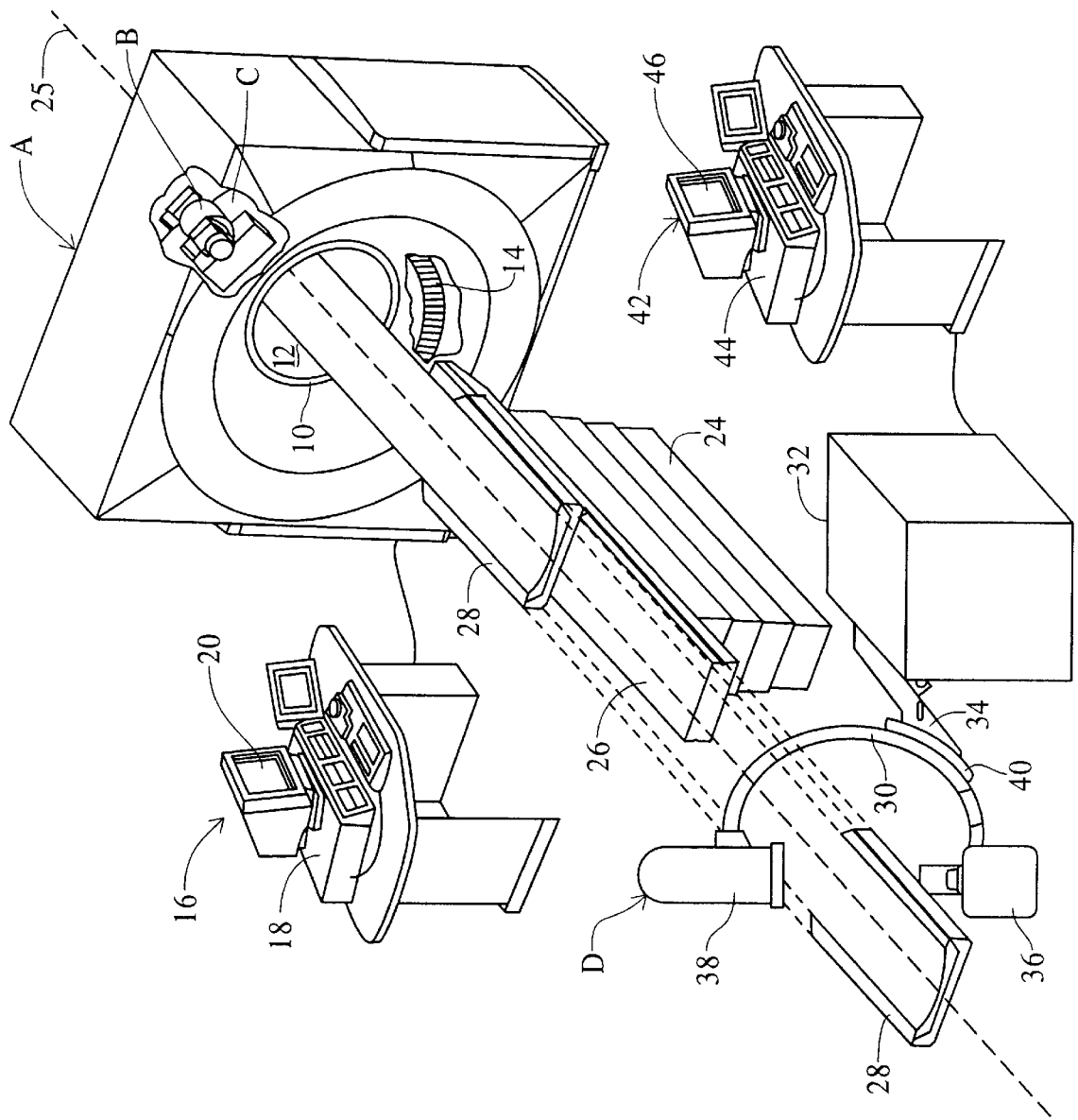
FIG. 1 is a perspective view of a longitudinally extending patient support having a CT gantry positioned at one end thereof and an angiographic system positioned at the other end thereof, remote from the CT gantry in accordance with a first embodiment of the invention.

With reference to FIG. 1, an exemplary diagnostic imaging system, such as a CT scanner, includes a floor-mounted, non-rotating frame member or gantry A whose position remains fixed during data collection. An x-ray tube B is rotatably mounted on a rotating frame member or gantry C. The stationary gantry A includes a cylinder 10 that defines a patient examination region 12. An array of radiation detectors 14 are disposed concentrically around the patient receiving region.

In the illustrated embodiment, the x-ray detectors are mounted on the stationary gantry portion such that an arc segment of the detectors receives radiation from the x-ray tube B which has traversed the examination region 12. Alternatively, an arc segment of radiation detectors can be mounted to the rotating gantry to rotate with the x-ray tube. The x-ray tube B and radiation detectors 14 comprise a diagnostic imaging subsystem of the diagnostic scanner.

A control console 16 contains an image reconstruction processor 18 for reconstructing an image representation out of signals from the detector array 14. Preferably, the image reconstruction processor reconstructs a volumetric image representation from radiation attenuation data taken along a spiral path through the patient. An exemplary reconstruction technique for spiral CT scanning is disclosed in U.S. Pat. No. 5,544,212, entitled "Spiral CT using Integrating Interpolator", which is assigned to the same Assignee as the present invention, and which is hereby incorporated by reference for all that it discloses.

A video monitor 20 converts selectable portions of the reconstructed volumetric image representation into a two-dimensional human-readable display. The console 16 includes tape and disk recording devices for archiving image representations, and also includes circuitry for performing image enhancements, selecting planes, 3D renderings, or color enhancements, and the like. Various scanner control functions such as initiating a scan, selecting among different types of scans, calibrating the system, and the like, are also performed at the control console 16.

The x-ray tube B includes an oil filled housing that has an x-ray permeable window directed toward the patient receiving region. An evacuated envelope is disposed within the housing and contains a rotating anode, such as a 7-inch anode, and a cathode or other electron source. High voltages, on the order of 150 kV applied between the rotating anode and the cathode, cause the generation of x-rays. The x-rays pass through the x-ray permeable window and across the patient receiving region 12.

Appropriate x-ray collimators 22 focus the radiation into one or more planar beams which span the examination region 12, as is conventional in the art. The console 16 includes circuitry for gating the x-ray source B to control patient dosage. A high voltage power supply is mounted on the rotating gantry for rotation with the x-ray tube.

A fixed patient table 24 is positioned adjacent the bore of the diagnostic scanner so as to extend from the examination region 12 in a first direction substantially along a central longitudinal axis 25 of the cylinder 10. A patient beam 26 is secured to an upper surface of the patient table 24. A patient couch 28 is slidably secured to the patient beam 26 for back and forth movement through the examination region 12 along the beam 26. It should be appreciated that at least the patient couch can be configured to pan laterally relative to a longitudinal axis of the gantry bore. The table 24, beam 26 and couch 28, cooperate to define a patient support which is adapted for movement through the examination region.

An angiography system D is positioned remote from the CT gantry A along the longitudinal axis 25 of the patient support. The angiography system includes a support member 30 that is movably secured to a frame 32 by a cantilevered arm 34. Alternatively, the support member 30 can be movably secured to a ceiling-mounted or overhead track (not shown).

In the illustrated embodiment, the support member 30 is a C-arm. An angiographic x-ray source or tube 36 is secured to a first end of the C-arm 30. Likewise, an x-ray detector 38 such as an image intensifier tube is secured to a second end of the C-arm 30. An examination region of the angiographic system is defined along the longitudinal axis 25 between the x-ray source 36 and detector 38.

The C-arm 30 is rotatably supported by a bearing assembly 40. The bearing assembly 40 permits the C-arm 30, and thus the x-ray source 36 and detector 38, to be rotated in a plane normal to the longitudinal axis 25 from an "under table" position shown in FIG. 1, to a lateral position on either side of the patient couch.

The C-arm 30 can move vertically and laterally relative to the patient support as the cantilevered arm 34 is pivoted relative to the frame 32, to permit easier access to the patient. Longitudinal image panning (i.e. along a patient's body) can be accomplished by automatically or manually driving the patient couch 28 in either or both directions along the rail 26. It should be appreciated that the bearing assembly 40 could permit the plane of the C-arm to rotate or tilt from an orientation normal to the longitudinal axis of the patient support to achieve approximately a 45° cranial/caudal angulation of the C-arm.

A control console 42 contains a controller 44 for controlling the operation of the angiographic system and for displaying a fluorographic image representation on at least one display monitor 46 from radiation attenuation signals received from the image intensifier tube 38. It should be appreciated that the control console 16 could be functionally integrated with the control console 42 to provide a single control console for controlling the operation of and viewing the resulting images generated by the angiographic system D and the CT scanner.

When performing an angiographic procedure with the diagnostic imaging system of the present invention, a patient is placed on the patient couch which is then manually, remotely, or automatically driven along the patient beam 26 to place the relevant portion of the patient within the examination region of the angiographic system D. The angiographic system is then utilized in a known manner to place a catheter in a given vessel. The vessel used depends on where the pathology is suspected to be. Once the catheter is in place, the patient couch is then manually, remotely, or automatically driven back along the beam 26 to position the patient within the bore of the CT gantry.

Once in position within the bore of the CT gantry, contrast material is then injected into the patient's blood stream through the catheter while gating on the CT scanner in a known manner. By using known spiral CT scanning techniques, a volumetric image representation can be reconstructed from radiation attenuation data taken along a spiral path through the patient. All of the two dimensional data is stored as a volume and later reconstructed into the final three dimensional rendering by the reconstruction process 18.

Thus, the CT scanner captures all possible angles of view with only one radiation exposure and one contrast injection to the patient. Further, by incorporating a CT gantry and CT spiral scanning techniques with an angiographic system, a volume of data can be obtained that can then be presented in any orientation in a variety of rendering modes including Maximum Intensity Projection, surface shaded display, or compositing.

In addition, by positioning an angiographic examination region and a common patient support along a longitudinal axis of a CT gantry bore, a patient can be safely moved from the angiographic examination region to the CT gantry bore without having to pivot the patient support or to move the patient from a CT suite to an angiographic suite.

For simpler procedures an intervenous injection could be made using an IV needle instead of having to thread a catheter into a given artery. With this approach, the contrast flows throughout the circulatory system to all parts of the body. However, there is a period of time where the contrast fluid is highly concentrated before it has a chance to become diluted by the blood pool. This is known as the bolus phase. The CT spiral acquisition can be timed so that the x-ray exposure coincides with the portion of anatomy where the bolus of contrast is flowing. In particular, the bolus could be timed and followed by manually panning the patient couch while watching a tomographic presentation on the system display 20.

An indexing system can be employed to accurately position the relevant portion of the patient into the bore of the CT gantry from the angiographic examination region. The indexing system may incorporate a stepper motor or a resolver to accurately position the patient.

Figure 2:
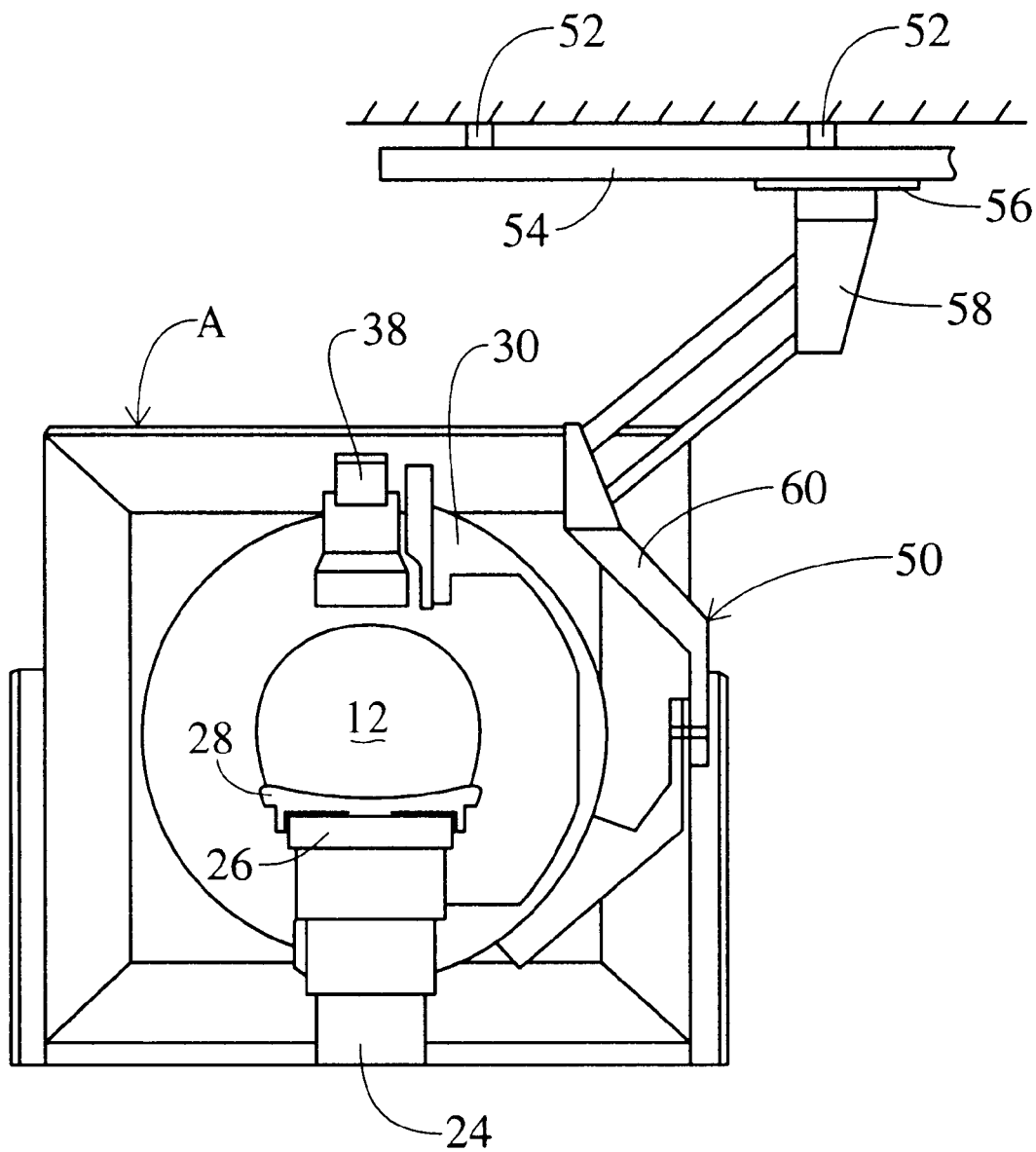
FIG. 2 is a end view of a patient support having a CT gantry and an angiographic system positioned together at a remote end of the patient support in accordance with a second embodiment of the invention.
Figure 3:
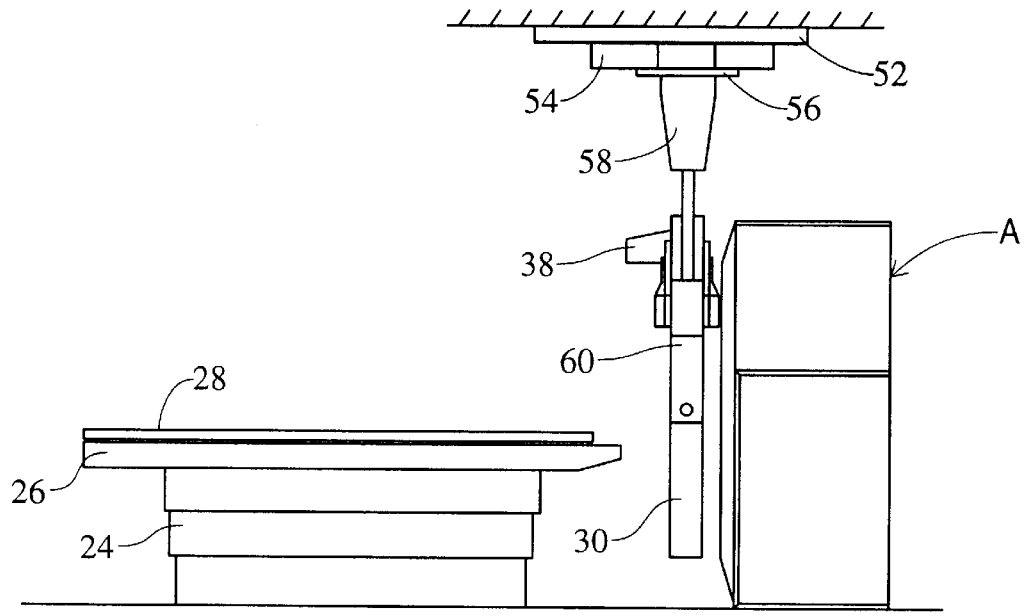
FIG. 3 is a side elevation view of the multi-modality diagnostic imaging system of FIG. 2.

Referring now to FIGS. 2 and 3, alternatively, the angiographic system D could be placed between the CT gantry A and the patient support, with the C-arm 30 suspended from an overhead or ceiling-mounted support system 50. The support system 50 includes first rails 52 and transverse rails 54 which are movable along the first rails 52. A trolley 56 is movably secured to the transverse rails 54 in directions transverse to the rails 52. A fixed or telescopic support arm 58 extends from the trolley 56. One or more cantilevered beams 60 extend from the arm 58 to support the C-arm 30. An advantage of having a ceiling mounted angiographic system is that there are no cables or trip points on the floor. Further, the C-arm 30 can be parked out of the way when not in use.

In the embodiment being described, the patient support can incorporate a conventional panning mechanism which permits an operator to horizontally move or pan the patient couch in either direction laterally or transverse to the longitudinal axis of the patient couch during angiographic procedures. That is, the patient support can include a four-way float, a panning handle, and a flat top insert (not shown). A transverse centering lock (not shown) can be activated by a switch on the panning handle to permit the patient couch to pan laterally during an angiographic procedure.

Figure 4:
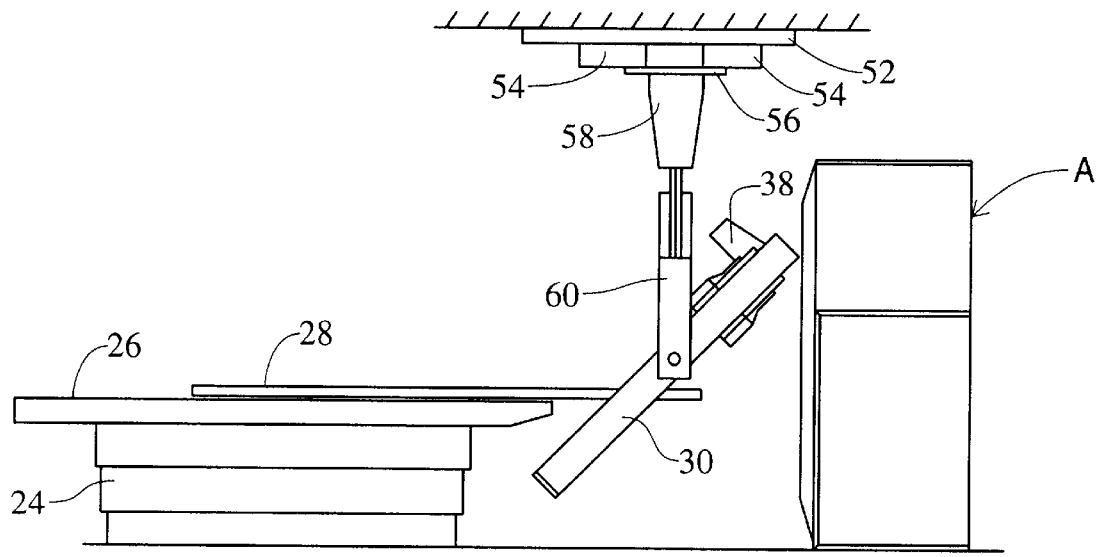
FIG. 4 is a side elevation view of the imaging system of FIG. 2 with a C-arm of the angiographic system rotated to provide cranial/caudal views.

The patient support includes a slide mechanism which permits the patient table 24 to be moved away from the CT gantry to increase the space available for the C-arm between the CT gantry and the patient support during angiographic procedures. In particular, as shown in FIG. 4, by retracting the patient table away from the CT gantry, the plane of the C-arm 30 can rotate or tilt from an orientation normal to the longitudinal axis of the patient support to achieve up to an approximately 45° cranial/caudal angulation of the C-arm. The retractable patient support permits switching between CT and angiographic procedures without disturbing the patient.

Referring now to FIGS. 5–8, the slide mechanism includes a number of linear bearings 60 mounted to the base of the patient table 24 which cooperate with a suitable number of bearing blocks 62 secured to a floor-mounted plate 64. The linear bearings 60 and bearing blocks 62 may include complementary locking portions such as "dovetails" which slidably secure the linear bearings, and hence the patient support, to the floor plate 64.

A power cable extension/retraction system for driving the patient couch 28 includes a J-shaped pan or tray 66 secured to the bottom of the patient table 24 between the linear bearings 60. The tray 66 includes a first side wall 68 having a flange 70 which secures the tray 66 to the patient table 24. An upper free end of a second side wall 72 is spaced from the bottom of the patient table to define a gap therebetween. An upright, L-shaped bracket 74 extends from the plate 64. One leg of the L-shaped bracket extends over the upper end of the side wall 72 within the gap.

A bundle of power, data, and/or control cables or wires 76 feed up through an aperture 78 in the plate 64. The cables 76 are guided through the gap between the side wall 72 and patient table 24 and into the tray 66 by the L-shaped bracket.

The cables 76 define a take-up loop 80 which rests within the tray 66. As the patient couch 28 is driven along the patient table, the take-up loop extends and retracts as the cable is fed to and received from the patient couch. The slide mechanism can include a power drive or power assist feature, or can be manually operated to retract the patient support. Further, sensors, locks and detents can be included to insure positive locking of the patient support in the different positions.

It should be appreciated that the slide mechanism and power cable retraction system permit the C-arm 30 to have a full range of motion during angiographic procedures without any exposed rails on the floor. That is, the slide mechanism and power cable retraction system is completely contained within the existing footprint of the patient support and therefore does not create a trip hazard to medical personnel. Further, the linear bearings 60 and bearing blocks 62 cooperate along the length of the patient support to greatly enhance the rigidity of the assembly and to minimize deflection of the patient couch over its range of travel.

As with the multi-modality system of FIG. 1, the system shown in FIGS. 2–8 may incorporate an integrated or separate control consoles such as consoles 16, 42. Further, the one or more display monitors may be suspended from an overhead support, or may be positioned on one or more mobile carts.

Referring now to FIG. 9, an integrated controller E processes and combines imaging data acquired by the diagnostic imaging subsystem and the angiography subsystem of either multi-modality imaging system of FIG. 1 or FIGS. 2–8. A first volume memory 100 stores 3D volume data acquired during a volumetric imaging procedure performed with the diagnostic imaging subsystem. A 2D angiographic memory 102 stores 2D angiographic data acquired during an angiographic procedure performed with the angiographic subsystem D.

A digital filtering means 104 filters the data stored in the first volume memory 100 to remove data representing image artifacts and anatomical structures except for data representing vascular structures such as blood vessels. The digital filtering means can implement a conventional grey scale filtering algorithm to remove all data except for the data representing the blood vessel structures. The resulting data representing only the blood vessel structures is then stored in a second 3D volume memory 106.

An image projection processor means 108 inputs a projection angle signal from a position encoder 110 associated with the angiographic subsystem D. The projection angle signal is indicative of the projection angle or view that was utilized to acquire the angiographic data stored in the memory 102. The projection processor means 108 utilizes the projection angle signal to perform a data projection procedure on the 3D data stored in the memory 106. That is, a projection is taken through the 3D data stored in memory 106 at the same angle utilized during the angiographic procedure. The resulting 2D projection data set is stored in a 2D memory 112.

A first video processor 114 displays the resulting 2D projection image stored in the 2D memory 112 on a video monitor 116. Likewise, a second video processor 118 displays a 2D angiographic image on a video monitor 120. The 2D angiographic image is derived from the 2D data set stored in the memory 102. Both video monitors 116, 120 display the patient's vascular structures along with x-ray opaque, anatomical landmarks which were placed on the patient's body prior to performing the diagnostic imaging and angiographic procedures.

With the anatomical landmarks displayed on both video monitors 116, 120, an operator using an input device 122 such as a joystick, can position a cursor over each of the landmarks displayed on the monitors 116, 120 to record the coordinates such as Cartesian coordinates, of each landmark. The coordinates for each landmark are stored in a coordinate memory 124. A scale factor determining means 126 then implements a conventional scaling algorithm such as a Barrycenter algorithm to determine a scaling factor value from the landmark coordinates stored in the memory 124.

A scaling processor means 128 uses the scaling factor value to either scale up or scale down the 2D data set stored in the 2D memory 112. A superposition processing means 130 then combines or fuses together the scaled output from the scaling processor means 128 with the 2D angiographic data set stored in the angio memory 102 to generate a fused projection image. A video processor 132 displays the fused projection image on a display monitor 134. Alternatively, the fused image output from the scaling processor means 128 can be sent to either one of the video processors 114, 118 for display on one or both monitors 116, 120.

Alternatively, the scaling processor means 128 can scale up or down the 2D angiographic data set stored in the angio memory 102, and the superposition processing means 130 combines or fuses together the scaled output from the scaling processor means 128 with the 2D data set stored in the 2D memory 112 to generate the fused projection image. In either case, the integrated controller E combines, superimposes, or fuses a high-resolution 2D angiographic image generated by the angiographic subsystem D with a 2D projection image generated by the diagnostic imaging subsystem such as a CT scanner.

The invention has been described with reference to the preferred embodiment(s). Obviously, modifications and alterations will occur to others upon reading and understanding the preceding detailed description. It is intended that the invention be construed as including all such modifications and alterations insofar as they come within the scope of the appended claims or the equivalents thereof.

For instance, the present multi-modality imaging system can be used to perform other minimally invasive and/or interventional procedures such as abscess drainages, arterial portography, TIPS, catheter placement for organ assessment, needle biopsy, etc.

Having thus described the preferred embodiment(s), the invention is now claimed to be:

1. A multi-modality imaging system comprising:
   a computerized tomographic (CT) imaging subsystem including a frame and a bore through the frame defining a first examination region, the CT imaging subsystem further including means for generating and storing volumetric image representations of an object positioned within the first examination region;
   an angiographic imaging subsystem defining a second examination region, the angiographic imaging subsystem including means for generating real time angiographic image representations of an object positioned within the second examination region;
   the first and second examination regions being located along a common longitudinal axis of the multi-modality imaging system;
   a support including a couch for carrying an object between the first examination region and the second examination region;
   a processing means for combining a stored image representation from the CT imaging subsystem with real time image representations generated by the angiographic imaging subsystem to generate a combined output image representation;

a display which converts the combined output image representation into a human readable display.

2. A multi-modality imaging system, comprising:

a first diagnostic imaging subsystem including a frame and a bore through the frame defining a first examination region, the first diagnostic imaging subsystem further including means for generating and storing a volumetric image representation of an object positioned within the first examination region;

a second diagnostic imaging subsystem defining a second examination region, the second diagnostic imaging subsystem including means for generating real time angiographic image representations of an object positioned within the second examination region;

a support for carrying an object between the first examination region and the second examination region;

a processing means for extracting a two dimensional data set from the volumetric image representation generated by the first diagnostic imaging subsystem and combining the real time image representations generated by the second diagnostic imaging subsystem with the two dimensional data set, the processing means including:

an image projection processor for generating the two-dimensional data set representing a projection image through the volumetric image representation generated by the first diagnostic imaging subsystem, and a scaling processor for generating a scaled data set from at least one of the two-dimensional data set and the real time angiographic image representations generated by the second diagnostic imaging subsystem.

3. The imaging system of claim 2, wherein the first diagnostic imaging system includes a computerized tomographic (CT) imaging system and the second imaging system includes an angiographic diagnostic imaging system.

4. The imaging system of claim 2 further including:

a display for converting combined real time angiographic image representations and the two dimensional image representation into a human readable display.

5. A multi-modality imaging system, comprising:

a first diagnostic imaging subsystem defining a first examination region, the first diagnostic imaging subsystem further including a means for generating a volumetric data set representing a region of a patient positioned within the first examination region;

a second diagnostic imaging subsystem defining a second examination region, the second diagnostic imaging subsystem including a means for generating a two-dimensional angioqraphic data set representing a portion of a circulatory system of the region of the patient positioned within the second examination region;

a couch for carrying an object between the first examination region and the second examination;

an image processor system including:

an image projection processor for generating a two-dimensional projection data set representing a projection image through the volumetric data set generated by the first diagnostic imaging subsystem, a scaling processor for generating a scaled data set from at least one of the two-dimensional projection data set and the two-dimensional anqioqraphic data set generated by the second diagnostic imaging subsystem, a superpositioning processor for generating a combined diagnostic image from the scaled data set and the at least one of the two-dimensional projection data set and the two-dimensional angiographic data set; and a video monitor for displaying the combined diagnostic image.

6. The imaging system of claim 5, wherein the first diagnostic imaging system includes a computerized tomographic (CT) imaging system and the second imaging system includes an angiographic diagnostic imaging system.

7. A method of performing a diagnostic imaging procedure with a multi-modality imaging system including a frame defining a first examination region, a computerized tomographic (CT) imaging subsystem for generating volumetric image representations of a subject positioned within the first examination region, an angiographic imaging subsystem for generating angiographic image representations of the subject positioned within a second examination region, a subject support adapted for linear movement between the first and second examination regions, a processor for producing image representations from image data received from the computerized tomographic imaging system and the angiographic imaging system, the method comprising:

positioning the subject within the second examination region;

performing an anqiographic procedure with the angiographic imaging subsystem, the angiographic procedure including generating angiographic diagnostic images of the object while positioning a medical instrument within the subject;

positioning the subject within the first examination region;

performing a volumetric imaging procedure with the computerized tomographic imaging subsystem, the volumetric imaging procedure including timing an image acquisition to correspond to a flow of contrast agent introduced into the subject;

generating a combined output image by combining subsequent images generated by the angiographic imaging subsystem with an image generated by the tomographic imaging subsystem; and displaying the combined output image on a display monitor.

8. A method of performinq a diagnostic imaging procedure with a multi-modality imaging system defining a first examination reason, a computerized tomographic (CT) imaging subsystem for generating volumetric data sets of a patient positioned within the first examination region, an angiographic imaging subsystem for generating angiograqhic data sets of the patient positioned within a second examination region, a support adapted for moving the patient between the first and second examination regions, a processor for producing image representations from the data sets generated by the computerized tomographic imaging system and the angiographic imaging system, the method comprising:

a) positioning the patient in the first examination region;

b) acquiring a volumetric data set including timing image acquisition to correspond to circulatory flow in the patient;

c) generating a two-dimensional projection data set representing a projection through the volumetric data set acquired in step b);

d) positioning the patient within the second examination region;

e) generating real time angiographic data sets of the patient;

f) generating a scaled data set from at least one of the two-dimensional projection data sets and the two-dimensional angiographic data set generated in step e);

g) combining the scaled data set with at least one of the two-dimensional projection data set and the two-dimensional angiographic data set to generate a combined data set; and h) converting the combined data set into a human viewable image.

* * * * *